United States Patent [19]
Polaschegg

[11] Patent Number: 4,618,343
[45] Date of Patent: Oct. 21, 1986

[54] APPARATUS FOR PERITONEAL DIALYSIS

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 649,873

[22] Filed: Sep. 12, 1984

[30] Foreign Application Priority Data

Sep. 15, 1983 [DE] Fed. Rep. of Germany ....... 3333362

[51] Int. Cl.$^4$ .............................................. A61M 1/28
[52] U.S. Cl. ................................... 604/29; 210/321.3; 210/646
[58] Field of Search ............ 604/29; 210/321.3, 321.4, 210/646, 647

[56] References Cited
U.S. PATENT DOCUMENTS

| | | |
|---|---|---|
| 3,205,449 | 9/1965 | Udelson . |
| 3,791,767 | 2/1974 | Shill . |
| 4,081,372 | 3/1978 | Atkin et al. ........................ 604/29 X |
| 4,096,859 | 6/1978 | Agarwal et al. ............. 210/321.3 X |
| 4,190,047 | 2/1980 | Jacobsen et al. .................. 604/29 X |
| 4,338,190 | 7/1982 | Kraus et al. .................. 210/321.3 X |
| 4,412,917 | 11/1983 | Ahjopalo ........................... 604/29 X |
| 4,530,759 | 7/1985 | Schäl ............................ 210/321.3 X |

FOREIGN PATENT DOCUMENTS

| | | |
|---|---|---|
| 28371 | 5/1981 | European Pat. Off. .............. 604/29 |
| 2017408 | 10/1971 | Fed. Rep. of Germany ........ 604/29 |
| 2,838,414 | 3/1980 | Fed. Rep. of Germany . |
| 2947574 | 10/1980 | Fed. Rep. of Germany . |
| 3,115,299 | 11/1982 | Fed. Rep. of Germany . |
| 3131075 | 2/1983 | Fed. Rep. of Germany . |

OTHER PUBLICATIONS

Mr. A. Kraus Ph.D et al., "Ultrafiltration Peritoneal Dialysis and Recirculating Peritoneal Dialysis With a Portable Kidney", Dialysis and Transplantation, vol. 12, No. 5, May 1983, p. 385.

Primary Examiner—Anton O. Oechsle
Attorney, Agent, or Firm—Cushman, Darby & Cushman

[57] ABSTRACT

A peritoneal dialysis apparatus comprises a single lumen catheter through which in an intermittently operated circuit dialysis liquid is pumped from the peritoneal cavity of a patient and is then moved along in contact with a dialysis membrane, at which not only mass exchange but furthermore the withdrawal of ultrafiltrate is able to take place. On this membrane of the dialyzer a secondary dialysis takes place so that on the other side of the membrane dialysis liquid with an osmotically acting substance is moved in single-pass mode. Preferably the peritoneal dialysis circuit is made up of two dialyzers so placed that the one outlet of the first one is joined with a conventional dialysis apparatus and the outlet of the second dialyzer is joined with the catheter in the patient.

29 Claims, 5 Drawing Figures

APPARATUS FOR PERITONEAL DIALYSIS

BACKGROUND OF THE INVENTION

The present invention relates to peritoneal dialysis apparatus comprising at least one dialyzer that is divided by a membrane into first and second chambers, of which the first chamber is connected by a first circuit with a catheter and the second chamber is connected via a second circuit with a device for furnishing dialyzing liquid and in each circuit there is at least one pump.

In peritoneal dialysis the supplied peritoneal irrigating or dialyzing liquid has to be completely sterile, because otherwise there will be the danger of peritonitis. Such sterility problems are not normally to be encountered in hemodialysis since the blood has its own defense system that normally is able to take care of any intruding microbes. However there is no such defense system within the peritoneal cavity so that peritoneal dialysis has to take place under completely sterile conditions.

DISCUSSION OF THE PRIOR ART

There has been a suggestion in the periodical "DIALYSIS+TRANSPLANTATION", vol. 12, 1983, page 385 to so design a peritoneal dialysis apparatus that there was a circuit for the peritoneal dialysis liquid and a secondary, non-sterile dialyzing liquid circuit, the two circuits being kept separate from each other by a hemodialysis filter. At the membrane of the hemodialysis filter separation of the products of metabolism was to take place, that were contained in the peritoneal dialysis liquid, by diffusion through the membrane into the non-sterile dialyzing liquid. For this reason substances normally eliminated with the urine were constantly removed, without however removing water liberated osmoticaly through the peritoneum.

The peritoneal dialysis apparatus described in this publication has the following shortcomings:

The peritoneal dialysis circuit is joined up with a double bore catheter so that there is the undesired possibility of pumping liquid inwards and outwards at one and the same time, such liquid then not being able to be dialyzed. Because of this possibility that a quantity of liquid will be pumped out again right after it has been pumped in, dialysis in this machine, which is run continuously, is slowed down and the peritoneum is stressed more frequently and longer than would otherwise be desirable.

Furthermore in this publication a double bore catheter was to be used, that may only be utilized in this form of apparatus and not in other forms of treatment. In fact, the peritoneal dialysis apparatus described therein would not be able to be used for patients being subjected to continuous ambulant peritoneal dialysis (CAPD). Since in this method a single bore catheter is to be used, continuous operation of the peritoneal dialysis circuit is not possible. For this reason CAPD patients may not be connected with such an apparatus.

A further point in connection with the known apparatus is that no ultrafiltration is possible with secondary dialysis and furthermore there is the danger, in the case of the normal use of a single-pass unit, of infusion into the peritoneal dialysis circuit under certain condition so that the peritoneal cavity may well become filled with an additional quantity of liquid, this being highly undesirable.

Lastly the known machine is not sufficiently secured against a first error. The known apparatus is to continuously rid the irrigating liquid located in the peritoneal cavity of the products of metabolism, that is to say, it is not the whole of the irrigating liquid (as normal in CAPD) that is to be replaced after a certain time by fresh irrigating liquid. In this secondary dialysis however non-sterile dialysis liquid is moved along a hemodialysis filter, which it is not possible to inspect in operation to see if it is still liquid-tight. As a consequence of this a patient will necessarily be infected with microbes if there is any crack, as is not unlikely, that is to say a first error, in the hemodialysis apparatus. The outcome of this in turn is that such an apparatus may not be utilized for safety reasons.

SHORT OUTLINE OF THE PRESENT INVENTION

For this reason one aim of the present invention is to design a peritoneal dialysis apparatus of the sort initially defined in such a way that it may be used for CAPD patients as well while fully keeping to safety standards.

For attaining this and further objects the catheter has a single lumen or bore, a dialysis filter is so placed in the first circuit that the first chamber of the dialysis filter with an inlet and outlet duct and with the first chamber of the hemodialysis apparatus forms a closed circuit and the second chamber of the dialysis filter is joined up by way of a duct with the catheter, and a first pump is placed in the duct running to the dialysis filter and a second pump is placed in the duct coming from the dialysis filter and there is a storage vessel placed downstream from the second pump.

With such a peritoneal dialysis apparatus in keeping with the invention it now becomes possible to treat a CAPD patient, who has a single bore catheter available to him or her. The only connection of this peritoneal dialysis machine is joined up with the catheter of the patient, the patient then being supplied intermittently with a certain amount of liquid, which is let off again.

This apparatus is furthermore to be regarded as being proof against first error, and more specially against rupture of the membrane, because it is assumed to be highly unlikely that there will be two errors at the same time, that is to say two membrane ruptures in different filters.

The arrangement of such a second filter furthermore gives the additional benefit that a self-contained closed circuit is produced, which in the intact state is shut off from sources of infection and is for this reason to be regarded as well as being inherently sterile.

In consequence it is only necessary to take steps to see that the duct running from the second filter is kept sterile so that the patient may be joined up with the system again.

The apparatus for peritoneal dialysis of the present invention may be run by the patient himself in contrast to state of the art hemodialysis, because the system is so safe to operate that no supervision is required.

Furthermore proteins liberated through the peritoneum may be reliably retained and are kept in the peritoneal cavity, where they are able to be absorbed again.

As compared with CAPD treatment, the operation of the peritoneal dialysis machine of the present invention is very much cheaper so that more dialyzing liquid may be used and this in turn leads to the treatment time being considerably shortened. As a consequence of this, normally overnight treatment of the patient will be sufficient and on the following day the patient will be able to walk about.

Lastly it is furthermore possible for instable bicarbonate dialyzing liquid to be got ready straightway by the peritoneal dialysis machine and put at the disposal of the patient. As an outcome of this dialysis liquids containing lactate or acetate, which are less readily tolerated, may be replaced by dialysis liquid containing bicarbonate.

A further point to be noted is that with the peritoneal dialysis machine of the invention on the side where the dialysis liquid is prepared a corresponding amount of water may be withdrawn from the patient by a means for withdrawing ultrafiltrate, such operation being automatically controlled or not as may be desired.

In the non-automatically controlled form of the operation, the amount of ultrafiltrate taken from the patient is in line with empirically ascertained data, the rest of the amount of ultrafiltrate flowing into a bag after the connector has been undone.

On the other hand ultrafiltration may be undertaken in an automatically controlled manner, there being two possible forms of this in the present invention.

In the first form a pressure-responsive belt is used, that is placed round the abdomen of the patient. The amount of ultrafiltrate produced osmotically then causes an increase in girth and so a tension force in the belt, which is sensed by a suitable detector. This pressure-responsive detector then operates a control device with operates the ultrafiltrate pump.

On the other hand, in a different form of the invention use is made of the increase in the amount of water in the closed space made up on the one hand of the peritoneal cavity on the one hand and the closed extracorporeal circuit on the other hand. In this closed circuit space, as the amount of ultrafiltrate increases, the concentration of a marker or label substance is lowered, that is present in the dialysis liquid in a dissolved or suspended form and whose concentration may be ascertained by a detector. The concentration gradient that comes into being during peritoneal dialysis may be used for controlling ultrafiltration, it only being necessary to compare the original concentration and the concentration during treatment with each other. In a conventional comparator circuit it is possible for the ultrafiltrate pump to be worked until the original concentration of the substance to be measured is restored, viz. till the osmotically produced amount of ultrafiltrate has been pumped off.

As a useful feature of the invention the apparatus for preparing the dialysis liquid may have concentrate vessel, that contains the osmotically acting substance, more specially glucose, in a concentrated form. This osmotically acting substance is added to the dialysis liquid containing the conventional amounts of electrolyte in the desired osmotically active amounts and pumped into the hemodialyzer. In the latter there will be a balancing of the osmotically active amount through the membrane, such amount being partly absorbed through the peritoneum and for this reason has to be replaced. In contrast to this the marker substance used for control of the ultrafiltration should generally not be absorbed or modified in the peritoneal cavity.

Further details, features and benefits of the invention will be seen from the account now to be given of working examples of the invention using the figures.

LIST OF THE DIFFERENT VIEWS OF THE FIGURES

DETAILED ACCOUNT OF THE WORKING EXAMPLES OF THE INVENTION

Figure 1:
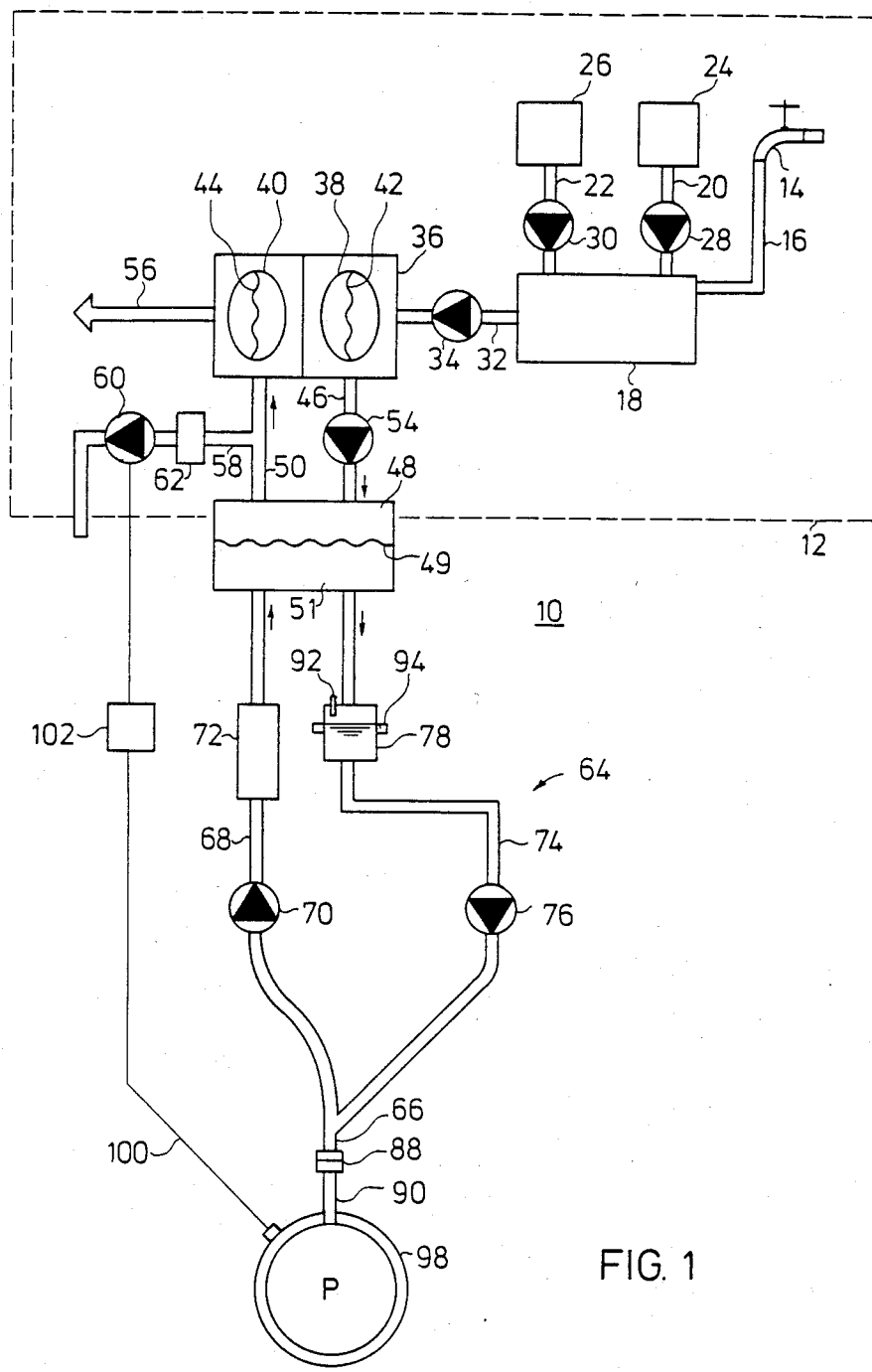
FIG. 1 is a diagram of a first working example of the invention in the form of a peritoneal dialysis apparatus.

FIG. 1 shows the peritoneal dialysis apparatus of the invention 10, that as a beneficial feature has a unit for preparing the dialysis liquid 12, as is marked in chained lines in FIG. 1. This unit 12 is best furnished with a conventional hemodialysis apparatus, as for example as marketed by the assignee under the designation A 2008. Such a hemodialysis apparatus is best operated in the so-called single pass mode, that is to say, the dialysis liquid is only run through the dialyzer once and then discarded. Furthermore this apparatus is best volumetrically controlled using the so-called balance chamber principle as is described in the German Offenlegungsschrift specification No. 2,838,414, the contents of such specification being expressly incorporated herein by reference.

In FIG. 1 this balancing apparatus is diagrammatically shown. The apparatus 12 accordingly has a fresh water connection 14, that is joined by a duct 16 with a unit 18 for producing the dialysis liquid.

The unit 18 is furthermore joined by way of ducts 20 and 22 with the vessel 24 containing the electrolyte concentrate or the vessel 26 containing the concentrate of osmotically active substance. There are pumps 28 and 30 in the ducts 20 and 22 respectively, such pumps supplying the concentrates alternately in portions, such alternation furthermore controlling the balancing chambers as will be described below. The pump 30 for the concentrate of the osmotically active substance, that is preferably glucose, may best be adjusted in keeping with the concentration of the osmotically active substance desired in the dialysis liquid. Normally the concentration of glucose in the finished dialysis liquid will be in a range from 1.5 to 4.25%, corresponding to a theoretical osmolarity of about 358 to 516 mosm/l. In a way similar to the electrolyte solution concentrate, the concentrate of the osmotically active substance is diluted by a factor of 35, viz. the concentrate has to be enriched by the corresponding factor.

Furthermore the unit 18 has a conventional warming and degassing device, not shown, for the dialysis liquid.

The unit 18 is furthermore connected via duct 32, running through a pump 34, with the balancing chamber group 36, that is only diagrammatically shown in FIG. 1. It is best for the balancing chamber group to have two balancing chambers 38 and 40, that are divided by a membrane 42 and 44 into the respective balancing chamber halves. The manner of operation of these balancing chambers is also described in the said German Offenlegungsschrift specification No. 2,838,414.

The balancing chamber group 36 is joined up by way of a duct 46 with the inlet of a dialyzer 48, whereas the outlet of the dialyzer 48 is joined by a duct 50 with the balancing chamber group 36 so that a closed circuit is produced between the one chamber of the dialyzer 48 by way of the ducts 46 and 50 with the balancing chamber group 36.

During operation, the balancing chambers 38 and 40 are each either filled with the dialysis liquid and at the same time emptied of spent dialysis liquid, or the chamber that has already been charged with dialysis liquid is emptied by a pump 54 with the duct 46 running through it, the spent dialysis liquid then being returned to the other half balancing chamber. As soon as the membranes 42 and 44 have come up against the wall of the balancing chambers 38 and 40, there is a switch over using valves (that are not shown) so that the manner of operation of the balancing chambers is reversed as well. The removal of the spent liquid is in this respect by way of the duct 56.

In order to remove ultrafiltrate from this closed system the duct 50 is joined with a duct 58, running through an ultrafiltrate pump 60. The liquid so removed is best degassed in a degassing vessel 62, as is also described in the said German Offenlegungsschrift specification No. 2,838,414. Accordingly the function of the ultrafiltrate pump is best a positive displacement one, a piston or a membrane pump being preferred.

The dialyzer 48 is best in the form of a conventional hemodialyzer, for example in the form of a plate or hollow fiber dialyzer. Such dialyzers have a cut-off limit at a molecular weight of about 5,000 to 10,000 and for this reason, in their pristine condition, will bar the access of bacteria from the side of the membrane supplied with the freshly prepared dialysis liquid, that is to say from the side of the unit 12. For this reason the dialysis liquid does not have to be completely sterile, because the sterilizing filtration may take place at the hemodialyzer. On the other hand a conventional hemofilter may be used, whose cut-off limit is under the molecular weight of albumin (60,000) so that this protein does not have to be eliminated, as would be a shortcoming in CAPD treatment.

There is a circuit 64 on the other side of the membrane of the dialyzer 48, such circuit only being charged by way of a duct 66. The circuit 64 has a duct 68 branching from the duct 66 and having its other end joined with the inlet of the dialyzer 48. This duct 68 runs through a pump 70, preferably a peristaltic one, and a storage vessel 72.

On this side of the membrane there is a further duct 74 running from the dialyzer 48, such duct also running through a pump 76 and if desired a drop chamber 78.

This duct 74 runs back to the duct 66 so that a Y-junction transition is formed between the duct 66, the duct 68 and duct 74.

The storage vessel 72 may best be a flexible-walled vessel, whose wall may be collapsed. Such a vessel may for example be in the form of a bag.

In a first possible form of the invention, the wall of this storage vessel 72 is able to be collapsed, but it is not able to be expanded or inflated. Such a vessel will be seen in the U.S. Pat. No. 3,791,767 for example, such disclosure being incorporated herein by reference.

Figure 2:
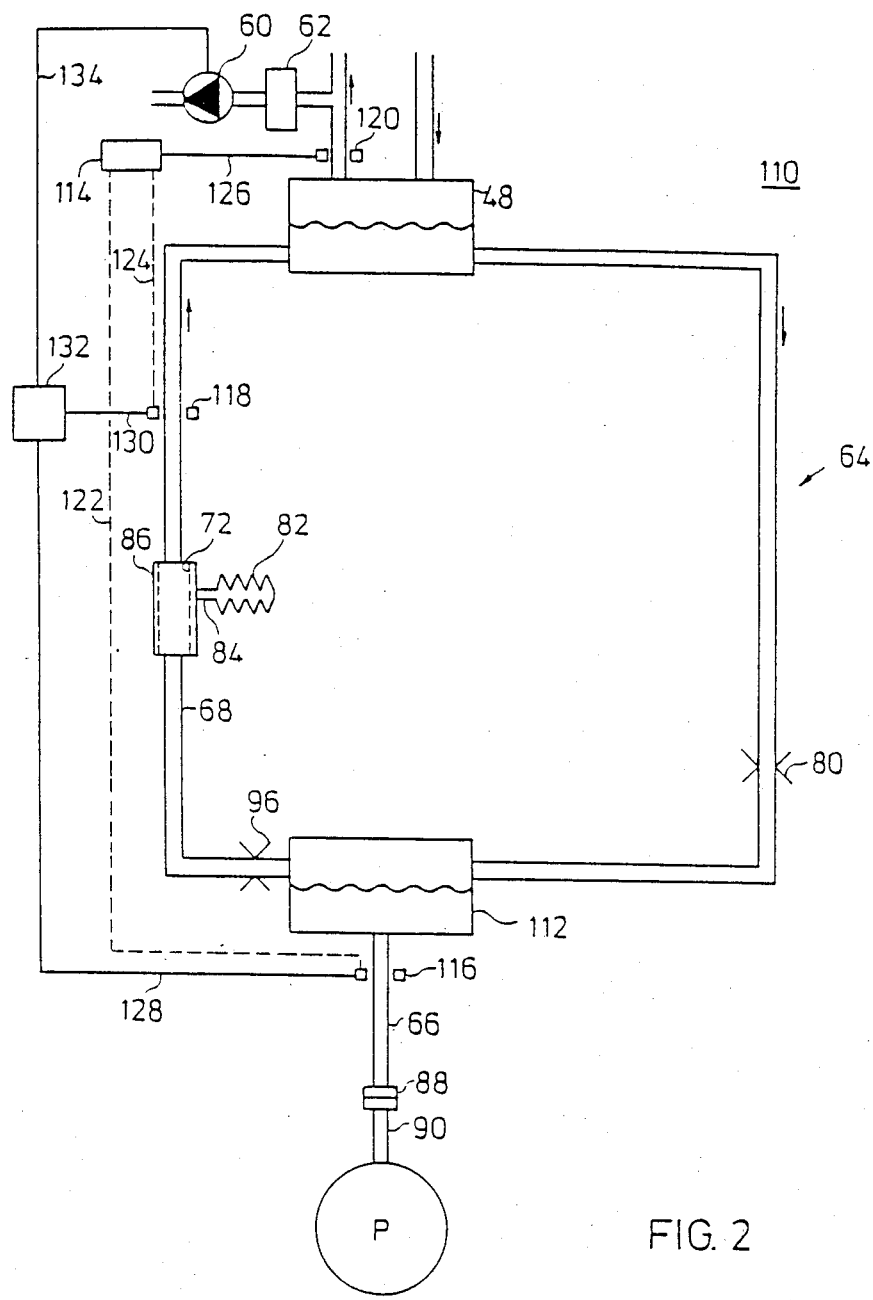
FIG. 2 is a diagram of a second working example of the peritoneal dialysis apparatus of the invention.

In a second form of the invention, the wall of the collapsible storage vessel may be elastically stretched or expanded so that when the deforming force no longer acts, it will return to the form it had in the first place. It is for this reason that in place of the pump 76, that is used to empty the storage vessel 72, it would be possible to have a clamp 80 as shown in figure 2, working 180 deg. out of phase with the pump 70. Such a storage vessel 72 with a stretchable wall is for example disclosed in the German Offenlegungsschrift specification No. 3,131,075, which in this respect is expressly incorporated by reference herein.

When charged, the storage vessel 72 is to contain about 300 to 700 and more specially about 500 ml of dialysis liquid. Accordingly a storage vessel with a non-stretch wall will have to have at least such an interior volume, whereas a storage vessel with an elastically stretching wall may have a smaller interior volume, for example with a volume smaller by a factor of 2 to 3.

In place of the pump 70 a useful effect is to be gotten by having a bellows pump 82, as will be seen in FIG. 2. By way of a duct 84 the bellows pump 82 is joined with the housing 86, in which the storage vessel 72 is placed. This storage vessel 72 may have a non-stretch or unexpansible wall, although it is preferred to have a stretch wall. Whereas the first form is described in the U.S. Pat. No. 3,791,767, the second form is to be seen in the said specification No. 3,205,449. The disclosures of these specifications are again incorporated by reference herein in relevant respects.

As the reader will be able to see form FIG. 1, the duct 66 may be joined with the catheter 90 by way of a connector 88, such catheter 90 being implanted in the peritoneal cavity of the patient. On the other hand however it is possible for the duct 60 to be part of the catheter 90 itself, it being for example welded thereto so that there is no connector 88. In such a case however the duct 66 is able to be reversibly separated from the catheter using a special hose welding machine.

A connector system which may be used as the connector 88, is to be seen for example in the German Offenlegungsschrift specification No. 2,947,574, whose relevant disclosure is incorporated by reference herein.

By opening the connector 88 and corresponding closing of the connector parts it will be seen that is possible for the patient to be disconnected from the peritoneal dialysis apparatus 10 and joined up again therewith for further treatment when desired.

ACCOUNT OF OPERATION OF PERITONEAL DIALYSIS APPARATUS OF FIG. 1

First the peritoneal cavity of the patient P is filled with sterile dialysis liquid, as is for example the case with CAPD. To this end a bag containing the necessary amount of dialysis liquid is joined up by way of the connector 88 with the catheter 90 and emptied. Nextly it is disconnected and the patient is joined up by way of the connector 88 with the peritoneal dialysis device 10, that is already completely filled with the right dialysis liquid.

The dialysis liquid is firstly prepared in the unit 12 using concentrates and tap water and supplied in a warmed and degassed condition by the pump 34 to the balancing pump group 36. This balancing pump group 36 supplies the prepared dialysis liquid under full volumetric control through the dialyzer 48 without at first any vacuum being applied for causing ultrafiltration. Because of the non-compressible nature of the dialysis liquid there is therefore no drawing off of water from the whole closed system.

On the other side of the membrane 49 the dialysis liquid circulating in the peritoneal cavity is intermittently circulated by firstly turning on the pump 70, whereas the pump 76 is stopped or the clamp 80 shuts the deduct 74. For this reason the pump 70 draws a corresponding amount of liquid, as for example 300 to 700 and more specially about 500 ml, and pumps this liquid into the storage vessel 72. After this the pump 70 is turned off so that it shuts off the return path through the duct 68. On turning off the pump 70, the pump 76 is started or the clamp 80 is opened. After this the liquid present in the storage vessel 72 is pumped off and moved along in contact with the membrane 49 of the dialyzer 48. Because the peritoneum is used as a primary membrane and has yielded up the corresponding metabolites into the liquid within the peritoneal cavity from the blood, these metabolites are also moved along in contact with the dialysis membrane 49 and are made to diffuse by the concentration gradient through the membrane 49 and then are conveyed with the spent dialysis liquid through the duct 56 to the waste connection. After the diffusion treatment the dialysis liquid goes into a drip chamber 78, that is best fitted with a hydrophobic filter 92 for separation of the air and to keep the liquid level at a given height in the drip chamber 78. Such a drip chamber is described in the German Offenlegungsschrift specification No. 3,115,299, whose relevant disclosure is hereby incorporated by reference. A sensor 94 is placed on the outer face of the drip chamber in order to control the level in the drip chamber 78. If the liquid goes below a certain level, the pump 76 is turned off or the clamp 80 is shut.

On the other hand the drip chamber 78 does not necessarily have to be present. If it is not present, the pump 76 is run until the storage means 72 is completely emptied. After the dialysis liquid has been pumped back into the peritoneal cavity of the patient, the pump 70 or 82 is turned on again to draw off dialysis liquid again. If a pump 82 is mounted on the outside of the storage vessel 72, there will be a clamp 96 near the Y-like junction (see FIG. 2). This clamp 96 has the same effect as the stationary pump 70, that is to say it blocks the duct 68.

The above manner of operation is only for cleaning the patient's blood to get rid of metabolites and not for removal of water, that is only possible by ultrafiltration.

Because vacuum may not be applied to the patient as such, the removal of water is primarily by osmosis, the osmotically acting substance contained in the dialysis liquid, as for example glucose in the desired concentration, causing this ultrafiltration. The water collecting in the peritoneal cavity causes the patient's girth to increase so that the belt 98 responding to such change in girth may be used for regulation of the ultrafiltration. This belt 98 responding to the girth is joined electrically by way of a wire 100 with an ultrafiltration regulator 102, that for its part controls the ultrafiltrate pump 60, which therefore takes a certain amount of dialysis liquid from the peritoneal cavity in keeping with the signal from the belt 98 and so produces vacuum on the membrane 49 so that the same amount of dialysis liquid is taken from the circuit and, in connection therewith, from the peritoneal cavity.

It is to be added in this respect that the osmotically active substance, such as glucose, fructose, mannose, maltose or the like, is partly absorbed in the peritoneal cavity so that its concentration will steadily go down in CAPD. However with the peritoneal dialysis apparatus of the present invention such a drop in the concentration is barred, because the device 12 always supplied fresh dialysis liquid to the membrane 49, this leading, if there is a concentration gradient at the membrane 49, to a balancing of concentrations on the side of the peritoneal cavity. Therefore the osmotic concentration of the osmotically acting substance is generally kept up during the treatment.

In FIG. 2 the reader will see a further preferred form of the invention as a peritoneal dialysis apparatus 110, like reference numbers being used for parts with the same functions as in FIG. 1. Furthermore the device 12 for preparing and supplying dialysis liquid is omitted from this figure.

This more specially preferred form of the invention shown in FIG. 2 has, unlike the system of FIG. 1, a dialysis apparatus 112, whose outlet is connected with the one end of the duct 68 whose other end, as noted, is joined with the dialyzer 48. The inlet of the dialysis filter 112 is further connected with the end of the duct 74, that runs as far as the outlet of the dialyzer 48.

It will be seen from this that there is no longer the Y-like junction as in FIG. 1, that was formed between the ducts 68 and 74 on the one hand and the duct 66 on the other. This duct is joined with the filtrate outlet of the dialysis filter 112 so that a completely closed circuit is formed, that is made up of the duct 68, the first membrane chamber of the dialyzer 48, the duct 74 and the first chamber of the dialysis filter 112. It is only through the pores of the membranes of the dialyzer 48 and of the dialysis filter 112 that there is a connection for mass exchange and ultrafiltration. Preferably the sizes of the pores of these membranes are such that it is not possible for bacteria to make their way into the closed circulation. As noted earlier, a conventional dialyzer has a pore size of about 30 to 80 Å, whereas the dialysis filter 112 has the same pore size distribution or pore sizes that are very much greater. It is in this respect preferred to have dialysis filter 112, which has a very much larger mean pore size distribution, so that it for example will not let through molecules with a weight over at least 30,000. The upper limit for such pore sizes is a pore size that reliably keeps back microbes and is between about 0.2 and 0.5 microns is size.

One example for such a filter 112 is the hemofilter used for hemofiltration with a cut-off limit at a molecular weight of about 30,000, so that it will safely retain albumin with a MW of 60,000.

In the event of albumin not having to be retained, it is also possible to use cascade filters, that have a cut-off limit at a MW of about 200,000 to 400,000.

An arrangement in keeping with FIG. 2 is particularly preferred, which on the one hand has a hemodialyzer 48 with a cut-off limit at a MW of 5,000 to 10,000, and on the other hand a hemofilter as a dialysis filter 112, whose cut-off limit is at a MW of 20,000 to 400,000.

As already explained hereinbefore the system of FIG. 2 is a closed circuit one, which even in the unused condition, that is to say in the uncoupled condition, is inherently sterile. As a consequence the high-price filters 48 and 112 do not necessarily have to be replaced after each treatment.

It order to detect rupture of the membranes in the filters 48 and 112, a further form of the invention to be seen in FIG. 2 has a monitoring device 114, that cooperates with the sensors 116 and 118, and/or 120. These sensors are joined by way of ducts 122, 124 and 126 with the monitoring device 114.

In order to detect a leak in the membranes of the filters 48 and 112, the closed circuit, that is formed between the filters, has a substance that may be detected by these sensors 116 to 120, the size of the molecules of the substance being so large that they are not able to penetrate a membrane in the undamaged condition.

In the case of a conventional hemodialyzer the substances coming into question for this purpose are inulin, myoglobin, starch, hydroxyethylstarch, a polysaccharide such as a dextrane, that if desired may have a detectable molecular component. Such detectable molecular components are for example fluroescent molecular components or ones that absorb in the visible range and which are covalently bonded to the basic molecule, as for example dextrane blue. Such molecules are named labels.

As will be seen from FIG. 2 the detectors 116 and 120 only respond on the passage of such "tell-tale substances", this then causing the whole apparatus to be turned off. On the other hand the detector 118 may respond to a depeletion or fall in concentration of such substances, this also causing the apparatus to be shut down.

As noted earlier, it is necessary for the tell-tale substances to have such a molecular size that they are reliably retained by the membranes of the filters 48 and 112.

In keeping with a further form of the invention the substances are so selected that they are not able to pass the membrane of the dialyzer 48, but on the other hand may freely diffuse through the membrane of the dialysis filter 112. In such a case therefore the molecular weight of these substances is less than the cut-off limit of the dialysis filter 112. In consequence there is a diffusion of this substance through the membrane of the dialysis filter 112 into the peritoneal cavity so that basically it is not legitimate for this substance to be a toxic one. Furthermore this substance, in order to effect the aim of the invention, should not be absorbed by the peritoneum.

As noted earlier herein, the amount of water liberated by the osmosis in the peritoneal cavity is not readily ascertained so that ultrafiltration using the device 112 is prone to be complex. For this reason one will either proceed empirically, that is to say run the pump 60 at a certain rate of pumping, or utilize the pressure sensitive belt 98. In the working example now explained, the liquid present in the circuit 64 and the peritoneal cavity will be taken to be constant. Within a relatively short time the substance used to mark the osmotic water will become equally distributed in this amount of water so that using the sensor 115 and/or 118 an initial concentration $c_0$ of this substance may be ascertained. In this special case the sensors 116 or 118 are electrically joined by wires 128 and 130 with the ultrafiltration controller 132, which stores the value for the original concentration $c_0$ of the substance, that will steadily go down with progressive osmosis, if it is assumed that the absorption of this substance through the peritoneum is generally negligible. In consequence the value for the initial concentration $c_0$ is stored in the controller 132 and compared with succeeding changed values. After this, the controller 132 will turn on the pump 60 by way of the wire 134 till the concentration is back at the original value.

The detectors used in this case may be conventional fluorescence, absorption or transmission detectors, that are able to respond to even very small amounts of the substances. In other respects the manner of operation of the peritoneal dialysis apparatus 110 shown in FIG. 2 is the same as that of FIG. 1. In the case of FIG. 2 as will dialysis liquid is intermittently taken from the peritoneal cavity, using either the pump system with the pump 82 or the pump system as in FIG. 1 with the pump 70. A significant point in both cases is that the concentration of of the osmotically active substance in the entire system is constantly kept at a given value and so remains constant. This is an advantage over CAPD treatment, in which the osmotically active substance becomes less strong in its effect, because of the dilution due to osmosis on the one hand and to the absorption of the osmotically active substance through the peritoneum on the other. Both these effects are countered in the peritoneal dialysis apparatus 10 or 110 of the invention, because on the one hand the water produced by osmosis is pumped off using ultrafiltration through the dialyzer 48 and on the other hand the concentration of the osmotically active substance is constantly controlled. However one point calling for attention in this respect is to see that there is no danger of hyperglycemic shock, as might be caused for example by the administration of excessive glucose.

In one special form of the invention the osmosis is only caused to take place at the start of the treatment, viz. after a certain time, within which the desired amount of liquid is liberated by osmosis, the glucose is eliminated from the whole dialysis liquid by halting the addition of glucose solution concentrate. The outcome of this is that the glucose disappears completely from the peritoneal circuit within a short time. Then the ultrafiltration control may be stopped. After this there will only be a removal of metabolites by diffusion and not by liberating water osmotically.

Figure 3:
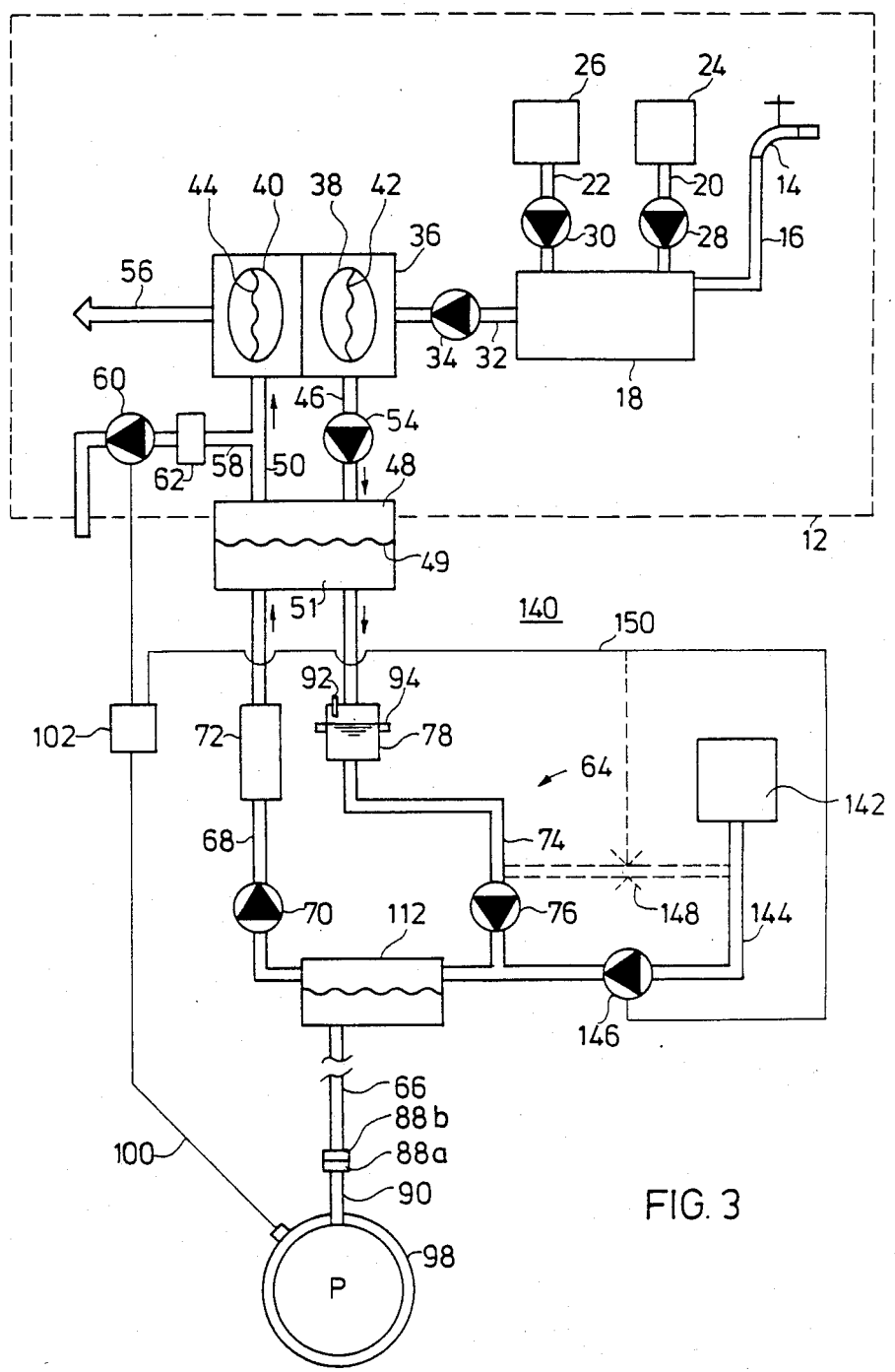
FIG. 3 is a diagrammatic view of a third working example of the invention, that by and large is based on the first working example.

In FIG. 3 the reader will see a further working example of a peritoneal dialysis apparatus 140, that gives particularly beneficial effects and generally uses teachings disclosed herein in connection with FIGS. 1 and 2. In this further form of the invention, like the form of FIG. 2, the dialysis filter 112 is joined by the ducts 68 and 74 with the one side of the membrane and by the duct 66 with the other side of the membrane so that once again, as was the case with FIG. 2, a closed circuit will be formed, that is made up of the ducts 68 and 74 and furthermore of the one dialysis filter chamber of the dialysis filters 48 and 112.

The closed circuit, like the system of FIG. 3, again has the pumps 70 and 76 in the ducts 68 and 74, that like the system of FIG. 1 are best in the form of peristaltic pumps.

With respect to the properties and the function of the filter 112, the reader is referred to the amount of FIG. 2 and with respect to the pumps 70 and 76 attention may be given to the account relating to FIG. 1.

This particularly preferred form of a peritoneal dialysis apparatus 140 to be seen in FIG. 3, may in addition be joined up with a vessel 142, that contains an additional liquid. Such an additional liquid is used in cases in which the dialysis treatment of the patient is to be improved. For example specially high-price medicaments such as insulin, chelate builders, adjuvants for the filtering properties of the peritoneum or the like may be supplied in a sterile condition in such a vessel 142.

This vessel 142 is joined up by way of a duct 144 with a point downstream from the pump 76 on the duct 74, the duct 144 running through a pump 146.

On the other hand it is possible for the duct 144 to be joined with the duct 74 at a point upstream from the pump 76, this being marked in chained lines in FIG. 3. In such a case there will be a clamp 148 in place of the pump 146 to shut off the duct 144 or to free it, as will be made clear later herein.

The additional liquid may be taken from the vessel 142 in the following manner.

When the pump 70 is running, that is to say the pump 76 is not running or in the form of the invention of FIG. 2, the clamp 96 is opened and the clamp 80 is shut down, the pump 146 will be turned off and the clamp 148 closed.

On starting up the pump 76 or opening the clamp 80 and turning off the pump 70 or shutting the clamp 96 the pump 146 is started at a set pumping rate. On the other hand the clamp 148 is so opened that the desired amount of liquid may be run off out of the vessel 142. However the use of a pump 146 is preferred, because it makes possible exact metering of the additional liquid.

As shown in FIG. 3, the pump 146 or the clamp 148 is joined up electrically by a wire 150 with the ultrafiltration controller or regulator 102. In keeping with one form of the invention in fact the additional supply of a liquid from the vessel 142 continuously increases the amount of liquid supplied to the patient, something that may lead to an undesired hyperhydration.

To keep this from happening the ultrafiltration controller 102 for its part operates the ultrafiltration pump in such a way that it draws off such an amount of liquid as equals the amount of additional liquid supplied by the pump 146. Accordingly, simply by the selection of the amounts of liquid to be supplied by the pump 146 the supply rate of the ultrafiltration pump is programmed with the outcome that the liquid balance is generally kept up on the supply of an additional amount of liquid from a vessel 142. It is to be noted in this connection that the ultrafiltration pump 60 naturally enough draws off this amount of liquid in addition to the amount that is to be ultrafiltered so that in the case of the present example the ultrafiltration pump has to be doubly programmed, viz. with respect to the amount that is in fact to be ultrafiltered and with respect to the amount that is to be supplied from the vessel 142 in addition and consequently has to be additionally withdrawn.

On the other hand the ultrafiltration pump 60 may naturally also be so controlled with the help of the belt 98 for controlling the withdrawal of ultrafiltrate that such programming will not be needed.

However it is best for the ultrafiltration pump 60 to be program-controlled as will now be described.

The amount of water passing through the peritoneum into the peritoneal cavity by osmosis depends generally on the osmolarity, viz. the content of the osmotically acting substance in the dialysis liquid and is furthermore specific to the patient. Accordingly after ascertainment of the amount of ultrafiltrate when using a dialysis liquid with a given composition, before peritoneal dialysis, it is possible for a patient to make a selection of the amount of osmotically active substance and so indirectly control the amount of ultrafiltrate to be produced. At the start of the peritoneal dialysis he or she will program the unit 18 for preparing the dialysis liquid, that will then be available. Furthermore when this is done the ultrafiltration pump 60 will be so programmed that generally the amount of ultrafiltrate coming from the patient will be drawn off. If the ultrafiltrate pump 60 withdraws a little more or a little less liquid from the peritoneal cavity, this will not be detrimental, because correspondingly less liquid will be let off on undoing the connector 88 from the peritoneal cavity.

Figure 4:
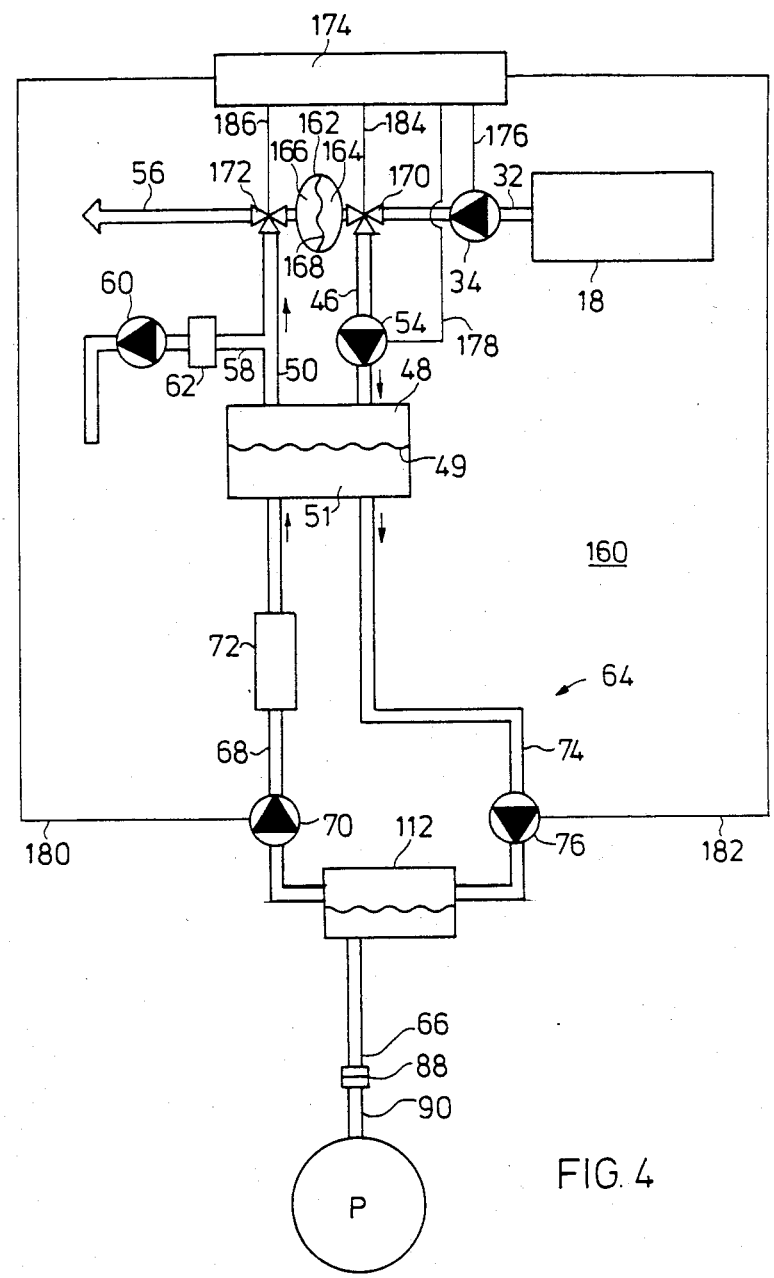
FIG. 4 is a diagrammatic view of a further example, in which only one balancing chamber is used.

In FIG. 4 the reader will see a further working example of a peritoneal dialysis apparatus 160, that utilizes important teachings of the peritoneal dialysis apparatus 140 of FIG. 3 so that once again the same reference numbers are used for parts having identical functions.

The peritoneal dialysis apparatus 160 of FIG. 4 unlike the peritoneal dialysis apparatus of FIGS. 1 to 3 has only one balance chamber 162, that is divided by a the membrane 168 into two balance chamber halves 164 and 166. There is again a duct 32 running from the balance chamber half 164, that is joined with the unit 18 for preparing the peritoneal liquid and which runs through a three-way valve 170. The duct 46 runs off from this three-way valve to the dialyzer 48.

The other half 166 of the balance chamber is again joined with the duct 76, that runs through a second three-way valve 172, whose other path is joined up with the duct 50.

Since the peritoneal dialysis apparatus 160 is only run intermittently, in keeping with a preferred form of the invention only balance chamber 162 is needed, that is filled or emptied respectively in the first cycle or stroke and in the second one is joined with the hemodialyzer in a closed circuit so that the same pumps peritoneal liquid.

To control this set of operations a controller 176 is present, that is joined with the pumps 34, 54, 70 and 76 via the ducts 176, 178, 180 and 182 and with the three-way valves 170 and 172 via the ducts 184 and 186.

In the first cycle the cycle controller 174 operates the peritoneal dialysis 160 in the following way.

The pump 70 is turned on and fills the storage vessel 72, while the pump 76 is turned off. Furthermore the three-way valves 170 and 172 are so switched that the balance chamber halves 164 and 166 are directly connected with the ducts 32 and 56. At the same time the pump 34 and the unit 18 are turned on, while the pump 54 is halted so that the filling of the balance chamber 162 is started, the membrane 168 being moved to the left in terms of FIG. 4 and as a result the spent dialysis liquid is forced out through the duct 56 to waste.

When the balance chamber 162 is filled with fresh dialysis liquid and the storage vessel 72 is filled with spent dialysis liquid, the cycle controller 174 switches over to the next or second cycle, the pumps 34 and 70 being turned off and the three-way valves 170 and 172 being so changed over that the balance chamber 162 forms a closed circuit with the dialyzer 48. In consequence the membrane is moved to the right under the effect of the pump 54, fresh dialysis liquid being pumped through the dialyzer and returning as spent dialysis liquid into the left balance chamber half 166.

As soon as the storage vessel 72 is pumped empty and the balance chamber 162 is filled with spent dialysis liquid, the cycle controller 174 changes over to the first cycle so that the filling operation is started over again.

The working examples to be seen in FIGS. 1 to 3, in which the dialysis apparatus 12 runs all the time, is to be contrasted with the example of FIG. 4 in which dialysis liquid is only supplied in the first cycle, whereas in the second cycle there is no unnecessary pumping of dialysis liquid. There is therefore a substantial saving in dialysis liquid, that eventually has a beneficial effect on the costs of treatment.

Figure 5:
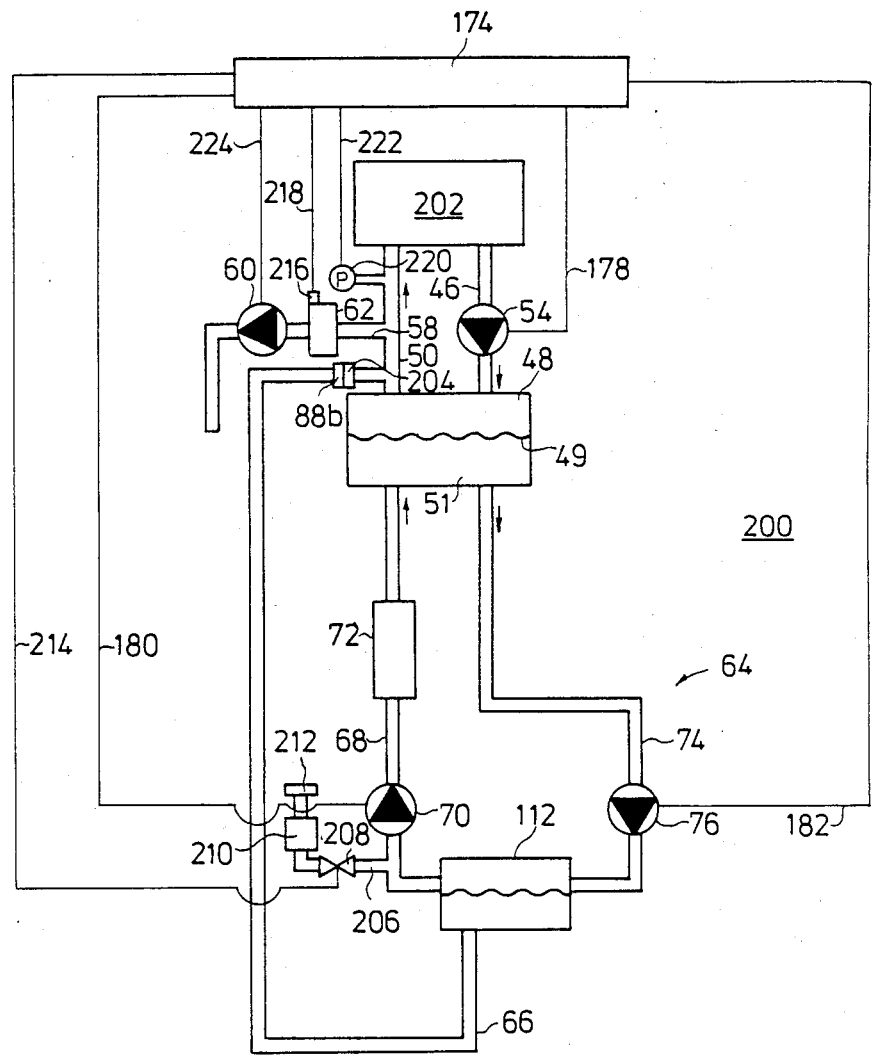
FIG. 5 is a diagram of a fifth working example of the invention in the form of a peritoneal dialysis device with a controller by way of which the customized filling, disinfecting and check program may be run.

FIG. 5 lastly shows a further working example of a peritoneal dialysis apparatus 200, in which it is possible to use not only a fully balancing peritoneal dialysis unit 12 as in FIGS. 1 to 3 but also a a single balance chamber 162, as is illustrated in FIG. 4. Accordingly the peritoneal dialysis apparatus 200 has a conventional unit for preparing the dialysis liquid which among other features has a disinfecting program. This unit 202 is joined through ducts 46 and 50 again with the dialyzer 48. The other side of the dialyzer 48 again has the circuit 64 as in FIG. 2, FIG. 3 or FIG. 4, which comprises pumps 70, 76 or 82 and a further dialyzer 112. On the other side of the membrane another duct 66 runs from this dialyzer 112 via a connector 88 to the patient as in FIGS. 1 to 4, or it may however, as in FIG. 5 return to the outlet duct 50. This outlet duct 50 has a corresponding connector part 204, that is used with the mating connector part 88b of the connector 88.

Therefore this connector part 204 corresponds to the connector part 88a, that is fixed on the end of the catheter 90. These two connector parts 204 and 88a are sealed off in a sterile condition till they are used.

It will be clear from FIG. 5 that this form of the invention consists of a peritoneal dialysis apparatus 200, that is not in operation. However before use such a peritoneal dialysis apparatus 200 must however be swilled out, disinfected, checked for leaks, swilled out again and then filled up before it may be used for dialysis again.

To this end the peritoneal dialysis apparatus 200 has an air vent duct 206 joined to the duct 68, such duct 206 being best joined up at a point directly upstream from the pump 70 with the pump 68. There is a valve 208 and an equalizing chamber 210 in this vent duct 206 and at the end there is a sterile and preferably hydrophobic air filter 212, through which, when the valve 208 is opened, the circuit 64 and the chambers, connected with this circuit 64, of the dialyzers 48 and 112 may be ventilated.

To make this possible the pumps 70 and 76 are again joined up by way of the ducts 180 and 182 with the cycle controller 174, that is again joined via ducts 214 with the valve 208.

Furthermore the degassing vessel 62 has a sensor 216 that causes a unit (not shown) to scavenge excess air from the degassing vessel 62, as is described in the German specification No. 2,838,414. This sensor 216 is joined by the duct 218 with the cycle controller 174 as well.

Furthermore the duct 50 is best furnished with a pressure sensor 220, that is joined via the duct 222 with the controller 174.

A description will now be given of the way in which the peritoneal dialysis apparatus 200 of FIG. 5 is swilled out using the controller 174.

In the swilling phase the unit 202 furnishes a swilling liquid, as for example water, but however the constant volume balancing function of the unit 202 is continued so that the circuit, that is made up of the unit 202, the ducts 46 and 50 and the dialyzer chamber of the dialyzer 48 is kept in existence so that the volume of the circuit may not be compressed because of the liquid therein.

While the valve 208 is kept shut, the pumps 70 and 76 are so operated that the pumping rate of the pump 76 is higher than the pumping rate of the pump 70 and in consequence vacuum is produced in the dialyzer chamber of the dialyzer 48, that is joined with the circuit 64 so that swilling liquid is pumped from the one chamber through the membrane into the other chamber of the dialyzer 48 and thence into the duct 74. Since the pump 70 is only able to clear the supplied liquid in part, the excess part is forced through the second filter 112 into the duct 66 and thence into the duct 50 so that the overall effect is that a pressure balanced system is is kept in being. In consequence the amount of liquid forced through the dialyzers 48 and 112 equals the difference in the volumes pumped by the pumps 70 and 76. This differential volume may be programmed into the controller 174.

After this swilling phase there is a disinfecting phase in which the peritoneal dialysis apparatus 200 is thoroughly swilled out with a disinfecting solution which is kept in it until it is used again in order to keep the filters and the ducts from becoming infected with bacteria.

To make this possible the unit 202 is switched over into the disinfection phase using disinfectant so that in place of a swilling liquid a disinfecting solution is supplied. The disinfecting phase takes place in the same way as the swilling phase just described so that details thereof may be gathered from the foregoing account.

After the disinfecting phase and right before further use of the peritoneal dialysis apparatus 200 the circuit 64 is checked for leaks. For this the controller 174 is joined electrically with the ultrafiltration pump 60 via a cable 224.

In this checking out phase, unlike the swilling and disinfecting phases, the pump 54 and the unit 202 are not in operation. For checking the circuit 64 the valve 208 is opened by the controller 174 and the ultrafiltration pump 60 is run at a given pumping rate so that the liquid in the circuit 64 made up of the ducts 68 and 74 and the dialyzer chambers joined thereto, is pumped off with the help of the ultrafiltration pump 60 and at the same time air is forced through the venting filter 212 into this circuit 64 so that in this pumping phase the pumping off of liquid hardly produces any vacuum at the pressure sensor 220. Once the circuit 64 is filled with air, the degree of vacuum slowly increases because of the compliance of the membranes of the dialyzers 48 and 112. The vacuum produced by the ultrafiltration pump 60 is however not able to pump the air, that has been pumped into the circuit 64, through the membranes that are wetted with water so that at the end of the compliance phase there will be a generally constant vacuum level between $-200$ and 600 mbar. These events may be controlled with the help of the pressure sensor and the controller 174 joined thereto, that after a given pumping time assumes that the circuit 64 is sealed and for this reason sterile, when a vacuum level having a certain relation to the atmospheric pressure is reached. Such a vacuum level will not be produced after a certain pumping phase if there is a crack in the membrane or a leak in the hose system. In this case the entire system of disposable parts will have to be discarded and replaced.

In a further form of the invention the level sensor 216 of the degassing vessel 62 is used in place of the pressure sensor 220. As indicated this level sensor 216 switches on a degassing pump (not shown) when the supply of excessive air causes the liquid level in the degassing vessel 62 to actuate the sensor 216. Therefore, inasfar as there are any membrane cracks in the dialyzers 48 or 112, the level sensor 216 will be operated and for this reason the controller 174 as well.

Furthermore in the pressure phase the pressure sensor 220 may be used for testing for leaks in the peritoneal dialysis apparatus 200, because in this phase at a given pumping rate events will be characteristic and able to be checked.

It is to be noted that during this pumping phase both pumps 70 and 76 have to be without any effct on the circuit 64, that is to say that have to be turned on.

At the end of the checking out phase there is a swilling and filling phase, in which the ultrafiltrate pump 60 is turned off but the valve 208 is kept open. However at first only the pump 76 is turned on, while the pump 70 is turned off. Again swilling liquid is supplied from the unit 202 with the aid of the pump 54. It is best for this unit 202 to be changed over from the closed and positive displacement mode as described hereinbefore to the open circuit mode so that the entire system may be filled without any trouble.

At this time the pump 76 is kept turned out till swilling liquid gets as far as the sterilizing filter 212. Then the pump 70 is turned on to scavenge the rest of the air from the circuit, the pumping rate of the pump 70 best then being less than the rate of the pump 76 so that downstream from the pump 76 a certain degree of vacuum will be produced and the excess air will be cleared through the sterilizing filter 212.

Furthermore the disinfecting solution in the duct 66 is kept pressurized and is for this reason cleared from this duct 66 and its place taken by swilling solution.

As soon as it is certain that the entire system is filled with swilling solution the unit 102 is switched over to dialysis liquid, that may be supplied with the unit 202 opened or closed.

Once the peritoneal dialysis apparatus 200 is filled with the dialysis solution, the duct 66 is disconnected from the duct 50 by undoing the connector 88b and joining it to the catheter 90 of the patient.

After this a certain amount of dialysis liquid is filled into the peritoneal cavity of the patient, this again being done with the unit 202 in the open position. Preferably only the pumps 54 and 76 are turned on by the controller 174, and these pumps fill a certain desired amount of dialysis liquid into the peritoneal cavity of the patient.

Once this liquid has been charged into the peritoneal cavity, the unit 202 is changed over to the closed, constant volume circuit mode and the peritoneal dialysis apparatus 200 is used in the way noted above for dialysis of the patient.

It is to be noted that the change-over from the closed to the open mode of a balanced system is described in the German Offenlegungsschrift specification No. 2,838,414, whose disclosure in this respect is expressly incorporated by reference herein.

It is furthermore possible for the circuit 64, made up of the dialyzer 48, the ducts 68 and 74 and the dialysis filter 112 together with the ducts joined thereto, to be marketed in an enclosure in the form of a self-contained and portable or hand-held device.

Lastly it is possible for the amount of peritoneal swilling liquid to be placed in the vessel 142 for an additional liquid, such swilling liquid being pumped into the peritoneal cavity directly so that the above-noted filling phase in the open system would no longer be needed.

I claim:

1. A peritoneal dialysis apparatus comprising:
   at least one dialyzer with a membrane dividing a space therein into first and second chambers,
   a single lumen catheter,
   a first circuit joining the said first chamber with said catheter,
   a second circuit,
   means for preparing dialysis liquid and joined with said second chamber via said second circuit,
   at least one pump in each of said first and second circuits,
   supply and outlet ducts,
   a dialysis filter joined with said supply and outlet ducts and having first and second chambers therein and so placed in said first circuit that with said supply duct and said outlet duct and the first chamber of the dialyzer the first chamber of the dialysis filter forms a closed circuit,
   a connection duct joining said second chamber of said dialysis filter with said catheter,
   a first pump placed in said supply duct,
   a second pump placed in said outlet duct,
   and a storage vessel joined with same at a point downstream from said second pump.

2. The apparatus as claimed in claim 1 comprising a means for withdrawing ultrafiltrate from the means for preparing dialysis liquid.

3. The apparatus as claimed in claim 1 comprising means for alternating operation of the first and second pumps, said pumps shutting off said supply and outlet ducts when said pumps are not in operation.

4. The apparatus as claimed in claim 3 wherein said first and second pumps are peristaltic pumps.

5. The apparatus as claimed in claim 2 wherein said means for preparing dialysis liquid is in the form of a constant-volume, balanced system.

6. The apparatus as claimed in claim 1 comprising a drip chamber connected in said supply duct downstream from the dialyzer, such drip chamber having a means for clearing air and a liquid level sensor.

7. The apparatus as claimed in claim 1 wherein said dialysis filter is placed in a circuit loop in which there is a substance whose molecular weight is above that of the cut-off limit of the dialyzer and of the dialysis filter.

8. The apparatus as claimed in claim 7 comprising a monitoring system including a monitoring unit and at least one sensor fitted to at least one of ducts selected from the group consisting of; a duct joined with said dialysis filter, said outlet duct, said duct joining said dialyzer with said dialysis filter.

9. The apparatus as claimed in claim 1 comprising a substance in the said circuit joining said dialyzer with said filter, whose molecular weight is greater than the cut-off limit of the dialyzer but smaller than the cut-off limit of the dialysis filter.

10. The apparatus as claimed in claim 9 wherein said sensors are electrically joined with an ultrafiltration controller for control of the ultrafiltration pump on the basis of a comparison with the initial concentration of the substance for control of the ultrafiltration.

11. The apparatus as claimed in claim 1 comprising a vessel for additional liquid and a further duct joining same with said supply duct, said further duct having means for controlling the flow of liquid therethrough and being operated synchronously with said first pump.

12. The apparatus as claimed in claim 11 wherein said flow controlling means includes a hose clamp.

13. The apparatus as claimed in claim 11 comprising an ultrafiltration controller, a wire electrically joining the said flow controlling means with said controller, and an ultrafiltration pump joined with said controller, said controller causing said ultrafiltration pump to pump an amount of ultrafiltrate equal to an amount of liquid taken from said additional liquid vessel.

14. The apparatus as claimed in claim 12 comprising an exit duct connected with said dialysis filter, means detachably joining said connection duct with said exit duct in a resting condition, a controller electrically joined with said first and second pump for so controlling said pumps in a swilling and disinfection phase that the pumping rate of said first pump is greater than that of said second pump.

15. The apparatus as claimed in claim 14 comprising a sterilely hermetic, hydrophobic filter, a valve, an intermediate duct joining said hydrophobic filter and said valve in series between said second pump and said dialysis filter, said valve being electrically joined with said controller, which is electrically connected with said ultrafiltration pump.

16. The apparatus as claimed in claim 15 comprising a degassing vessel, controlling means for switching said apparatus into a checking phase in which said controller opens said valve and turns on said ultrafiltration pump, a pressure sensor fitted to said exit duct and a liquid level sensor placed on said degassing vessel for ascertaining a time pressure relation.

17. The apparatus as claimed in claim 15 wherein said means for preparing dialysis liquid is designed to be switched, while in a filling phase, into an open mode of operation, the valve is open to let off air, the first pump is kept turned on till liquid emerges at said hydrophobic filter and subsequently said second pump is put into operation with a pumping rate below that of said first pump.

18. The apparatus as claimed in claim 17 wherein said controller so operates the means for preparing dialysis liquid that after connection of the connection duct with the catheter of the patient a certain amount of liquid is discharged through the said connection duct and the catheter.

19. The apparatus as claimed in claim 11 wherein said flow controlling means includes a pump.

20. The apparatus as claimed in claim 1 wherein said means for preparing dialysis liquid includes a balanced chamber, a feed pump and means for operation of same in a cycle in step with operation of said first and second pumps so that spent dialysis liquid is displaced and filling takes place in a first cycle stroke and in a second stroke the content thereof is pumped through the said dialyzer using said feed pump, said first pump being operated in said second stroke and said second pump being operated in said first stroke.

21. A peritoneal dialysis apparatus comprising:
at least one dialyzer with a membrane dividing a space therein into a first chamber and a second chamber,
said first chamber being in a first circuit connected with a single lumen catheter means and a storage means and comprising a means for supplying a dialysis fluid, and
said second chamber being connected via a second circuit with a means for preparing said dialysis fluid,
said second circuit comprising pump means and a dialysis filter divided by a membrane into a first chamber and a second chamber,
said first chamber of said dialysis filter being in said first circuit, and
said second chamber of said dialysis filter being connected with said catheter means.

22. Apparatus as claimed in claim 21 wherein the dialyzer is a hemodialyzer comprising a cut-off limit of about 5,000–10,000 Dalton (molecular weight).

23. Apparatus as claimed in claim 21 wherein the dialysis filter is a hemofilter with a cut-off limit of 20,000–40,0000 Dalton.

24. Apparatus as claimed in claim 21, wherein the first circuit comprises a substance whose molecular weight is above that of the cut-off limit of the dialyzer and of the dialysis filter.

25. Apparatus as claimed in claim 24, wherein the second chamber of the dialysis filter is connected via an exit duct with the catheter means, said exit duct comprises a first sensor, the first chamber of the dialysis filter is connected via an outlet duct with the first chamber of the dialyzer, said outlet duct comprises a second sensor, and said first and second sensors are connected with a controlling means for controlling said substance.

26. Apparatus as claimed in claim 24 wherein the second chamber of the dialyzer comprises an outlet duct comprising a third sensor connected with said controlling means.

27. Apparatus as claimed in claim 25 wherein the second chamber of the dialyzer comprises an outlet duct comprising a third sensor connected with said controlling means.

28. Apparatus as claimed in claim 21 wherein the first circuit comprises a substance whose molecular weight is above that of the cut-off limit of the dialyzer, but smaller than the cut-off limit of the dialysis filter.

29. Apparatus as claimed in claim 28 wherein the exit duct comprises a fourth sensor connected with a means for controlling the ultrafiltration by comparing the starting concentration of the substance and the concentration of the substance during the treatment of the patient.

* * * * *